US008840620B2

(12) United States Patent
Recoules-Arche et al.

(10) Patent No.: US 8,840,620 B2
(45) Date of Patent: Sep. 23, 2014

(54) SPINAL IMPLANT AND INSTRUMENT

(75) Inventors: Didier Recoules-Arche, Sainte-Adresse (FR); Robert Velez, Chateauroux (FR); Robert Lange, Paris (FR)

(73) Assignee: Coligne AG, Zurich (CH)

( * ) Notice: Subject to any disclaimer, the term of this patent is extended or adjusted under 35 U.S.C. 154(b) by 941 days.

(21) Appl. No.: 11/850,356

(22) Filed: Sep. 5, 2007

(65) Prior Publication Data

US 2008/0132901 A1  Jun. 5, 2008

Related U.S. Application Data (60) Provisional application No. 60/842,158, filed on Sep. 5, 2006.

(51) Int. Cl.
*A61B 17/56* (2006.01)
*A61F 2/44* (2006.01)
*A61F 2/46* (2006.01)

(52) U.S. Cl.
USPC ............................... 606/99; 623/17.16

(58) Field of Classification Search
USPC ............... 606/99, 247, 279; 623/17.11, 17.16
See application file for complete search history.

(56) References Cited

U.S. PATENT DOCUMENTS 5,586,989 A * 12/1996 Bray, Jr. ................. 606/160
5,817,062 A * 10/1998 Flom et al. .............. 604/174
5,861,041 A * 1/1999 Tienboon ............... 623/17.16
6,387,130 B1 * 5/2002 Stone et al. ............ 623/17.16
2002/0165550 A1 * 11/2002 Frey et al. .................. 606/85
2003/0139813 A1 * 7/2003 Messerli et al. ........ 623/17.11
2005/0027360 A1  2/2005 Webb et al.
2005/0038511 A1  2/2005 Martz et al.
2007/0016298 A1 * 1/2007 Recoules-Arche et al. ............. 623/17.11
2007/0299521 A1 * 12/2007 Glenn et al. ............ 623/17.11

FOREIGN PATENT DOCUMENTS

EP   1354572 A2   10/2003
EP   1430858 A1 *  6/2004  ............ A61F 2/44
EP   1653892    *  5/2006  ............ A61F 2/44
EP   1731116 A1   12/2006

* cited by examiner

*Primary Examiner* — Christian Sevilla
(74) *Attorney, Agent, or Firm* — Browdy and Neimark, PLLC (57) ABSTRACT

An instrument of an instrument set is used to insert an implant into a disc space. The implant comprises a first cage and a second cage and the instrument comprises a distal end configured to push the cage first inserted into the disc space laterally in its proper anatomical location. Said distal end of the instrument has a tip, which is curved and has a curved inner side configured to contact an outer curved side of the first cage. The instrument set allows the insertion of two cages through a relatively small incision in the interdisc space in a simple yet safe procedure.

6 Claims, 12 Drawing Sheets

SPINAL IMPLANT AND INSTRUMENT

BACKGROUND OF THE INVENTION

The invention relates to a spinal implant and instrument of an instrument set used to prepare a disc space and to insert the implant into said disc space.

A spinal implant and instrument set of this kind is disclosed in WO 2005/011539. The instruments include a distractor, a rasp and two guides. These instruments are used to prepare a space for the implant between adjacent vertebrae. The distractor is used to separate vertebrae during an insertion procedure. The implant, which is inserted into the disc space is a cage with a top configured to contact a first vertebra and a bottom configured to contact a second vertebra. The implant further comprises a curved anterior side and a curved posterior side.

A wedged cage walker is known to translate a cage inserted in the interdisc space laterally. With hammer percussion upon the wedge cage walker, a first cage is translated towards the midline, wherein a pedicle probe is used as a buttress for the wedge cage walker. Then a second cage is inserted through the same opening. Percussion upon the cage walker now translates both cages and opens the contralateral interspace.

In order to allow the surgeon to access the posterior elements, the anterior spine and deep spinal pathology were leaving the surrounding structures functionally intact, the ELIF method has been created as disclosed in the U.S. Provisional Application No. 60/688,331, filed Jun. 8, 2005, and corresponding U.S. Patent Publication 2007/00162978. The ELIF Lateral Trajectory Line originating from the anterior apophysis of the vertebral bode, running posterior and lateral oblique at about 30° across the superior vertebral endplate, past a position, just lateral to the superior facet and therefore the mamillary process, which is a caudal insertion point.

SUMMARY

The present invention now provides a spinal implant and instrument of an instrument set which comprises a first cage and a second cage and an instrument with a distal end configured to push the cage which is first inserted into the disc space laterally in a preliminary location, so that the second cage can be inserted, which adjusts the locations of both cages to the optimal anatomical location. two cages can be inserted into the interdisc space through the same small opening and can be positioned to provide stability and promote fusion of the vertebrae.

The instrument for positioning the first cage preferably has a distal end comprising a curved inner side configured to contact an outer curved side of the first cage. The distal end of the positioning instrument may have the shape of a curved finger.

According to a preferred embodiment of the invention, the cage to be inserted first is shorter than the second cage. The first cage can be inserted into the interdisc space with a well known inserter and than pushed laterally in its preliminary location using the positioning instrument. The second cage can then be inserted into the interdisc space using the natural curve of the Annulus fibrosus until the two cages mate bilaterally and adjust themselves due to pressure from the Annulus fibrosus.

According to a preferred embodiment of the invention the first cage and the second cage each have a curved interior matt face and a curved outer matt face and that the curved outer face of the first cage is configured to contact the curved inner face of the second cage. Preferably the second cage has a wedge shaped front part.

The positioning instrument preferably has a shaft with a straight proximal part, a tapered middle part and a curved distal part.

The instrumentation set preferably includes a spacer having a shaft with a straight proximal part, a tapered middle part and a cranked distal part. Preferably the instrumentation set comprises at least a positioning instrument, an inter-space spreader, a spacer and two cages.

DESCRIPTION OF THE PREFERRED EMBODIMENTS

Preferred embodiments of the invention are illustrated in the annexed drawings in which.

DETAILED DESCRIPTION

FIGS. 1 to 5 illustrate steps for a vertebral body of a vertebra implant into an interdisc space 9. The interdisc space 9 is the space between a spine and a not shown adjoining vertebra. The vertebra 7 is a lumbar vertebra. The implant comprises a first cage 2 and a second cage 3. These cages 2 and 3 are preferably made from a X-ray transparent material as for example PEEK, OSTAPEK or other polymers, but other materials such as titanium, titanium alloys or bone are possible as well.

Figure 7:
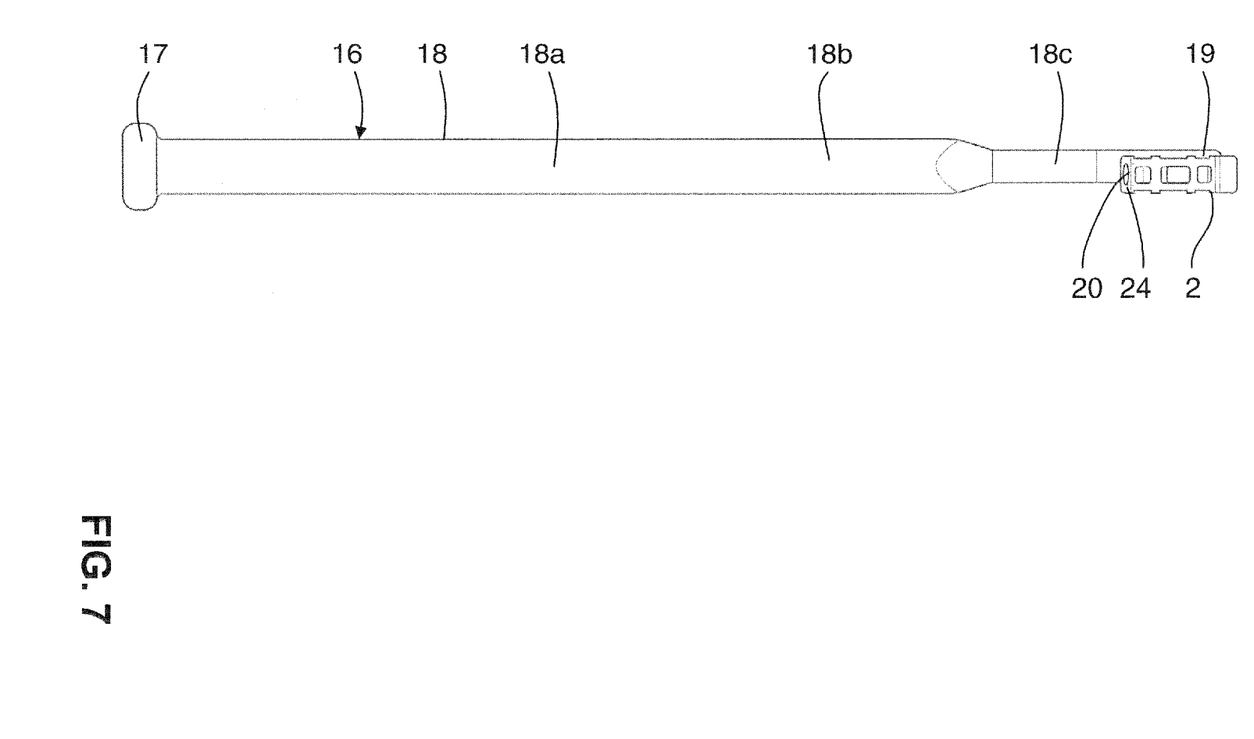
Figure 8:
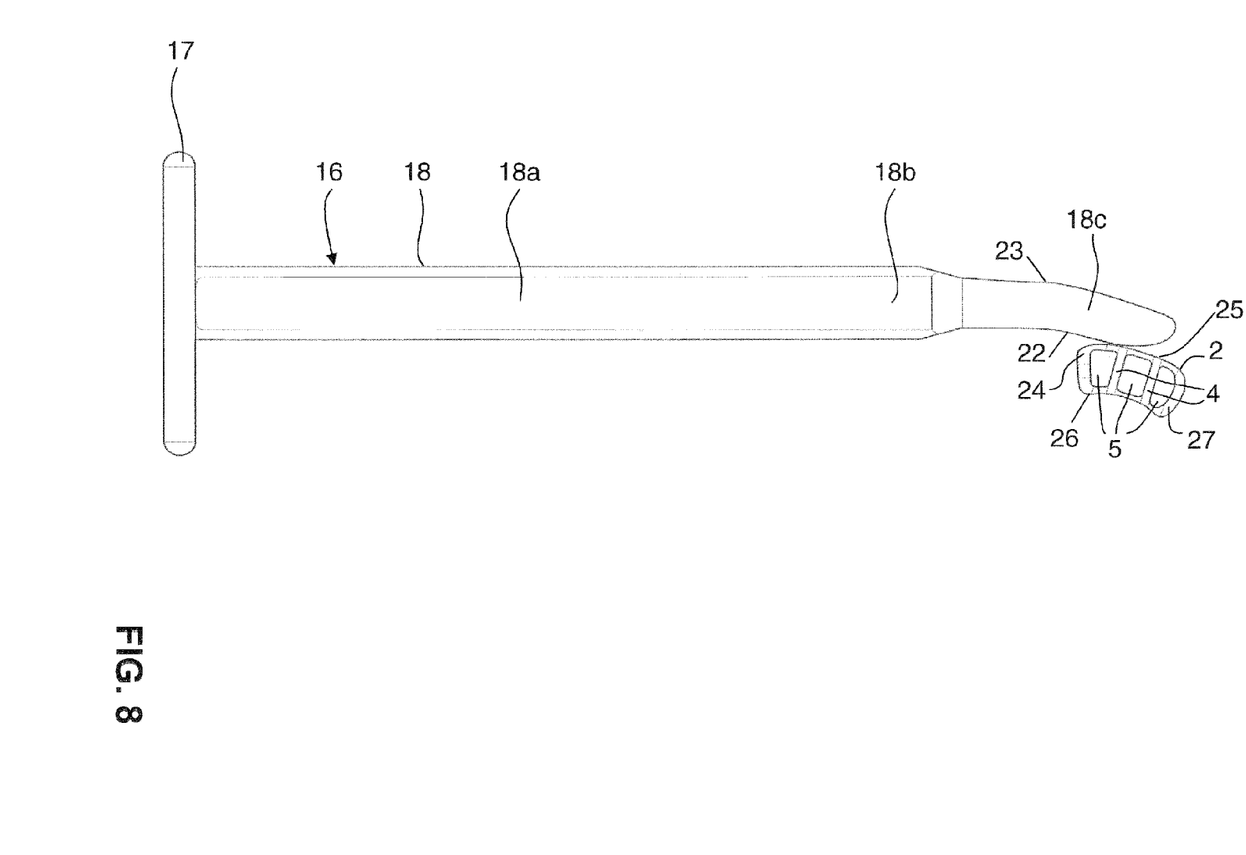

The cages 2 and 3 have openings 5 extending from bottom to top which can be filled with bone graft material. As shown in FIGS. 7 and 8, the first cage 2 is provided with a rear wall 24 which has a threaded opening 20 extending through this wall for receiving the threaded part of an inserter 34. Struts 4 extend between a convex curved outer side 25 and a concave inner side 26 as shown in FIG. 8. The first cage 2 is shorter than the second cage 3.

Figure 1:
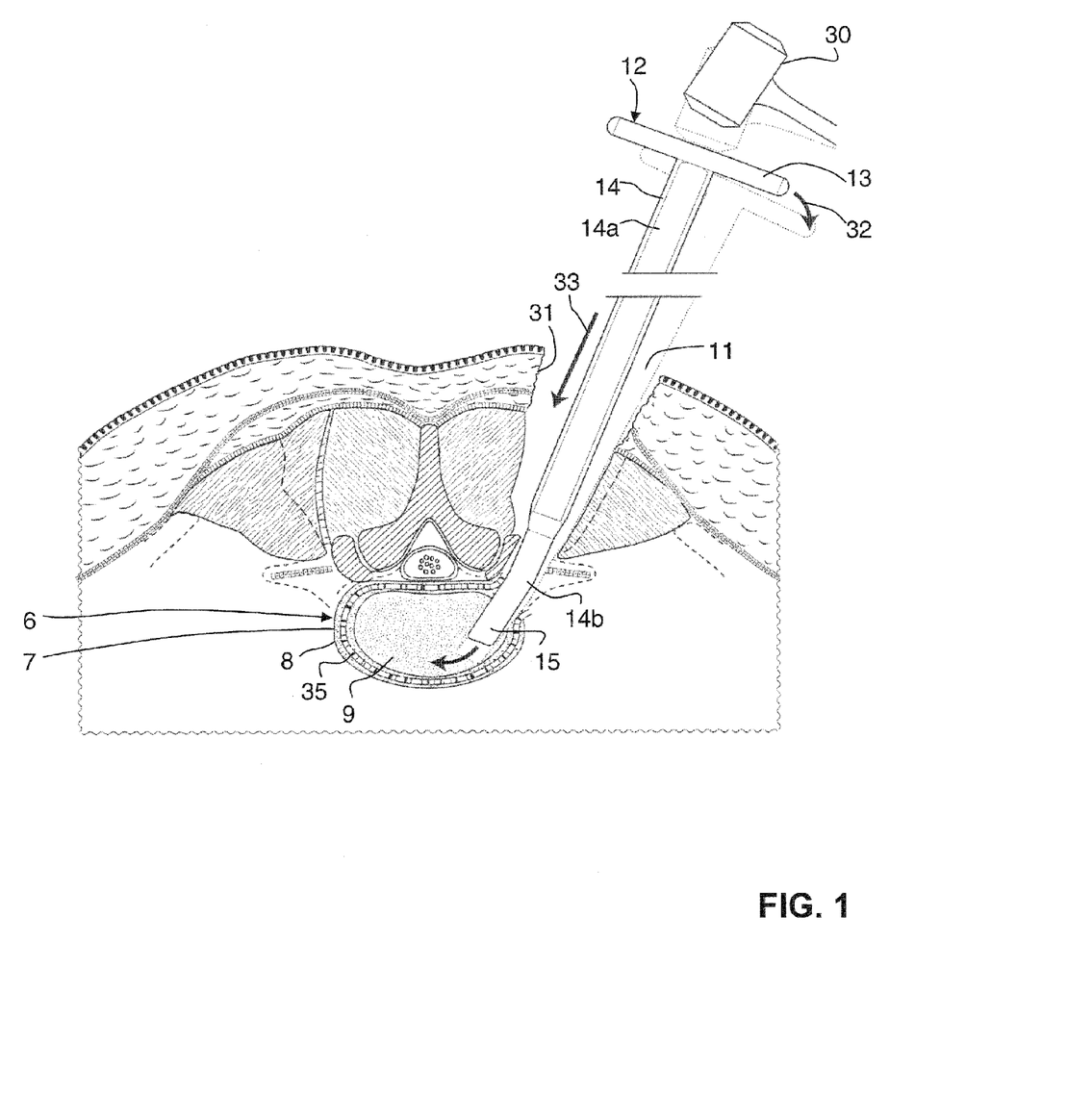
FIG. 1 a schematic view of an interspace spreader inserted into a interdisc space, FIG. 2 a) and b) schematic views of a first cage inserted into a interdisc space, FIG. 3 a) to c) schematic views of a positioning instrument, according to the present invention, during positioning of the first cage, FIG. 4 a) and b) schematic views during the insertion of a second cage, FIG. 5 a schematic view of the two cages inserted bilaterally into the interdisc space, FIG. 6 a perspective view of a positioning instrument according to the invention, inserted into a interdisc space, FIG. 7 a plane view of the positioning instrument, and FIG. 8 another plane view of the positioning instrument.

FIG. 1 shows a spacer 12 used to separate the vertebrae and to maintain a distance between the vertebrae which allows the insertion of the cages 2 and 3. The spacer 12 includes a handle 13 and a shaft 14, having a proximal part 14a, a tapered middle part 14b and a distal part 14c, and a tip 15. The spacer 12 is inserted with the distal part 14c and the middle part 14b in an opening 11 from the anterior apophysis of the vertebra 7. The opening 11 is made with an incision 31 and is running posterior and lateral oblique at about 20°-60° and preferably about 30° across the superior vertebral endplate. Through this opening 11 the first cage 2, the positioning instrument 16 and the second cage 3 are inserted as shown in the FIGS. 2 to 5. The instrument set for preparing the opening 11 and the interdisc space 9 may include any known and suitable instruments as for example scalpels, distractors, implant inserters, rasps and guides. The instrument set further may include various far reaching curettes, designed to clear the contralateral interspace. With these curettes, the cartilaginous endplate is removed without disrupting the subchondral bone, which assures optimal support for the bone graft and cages 2 and 3.

Figure 2A:
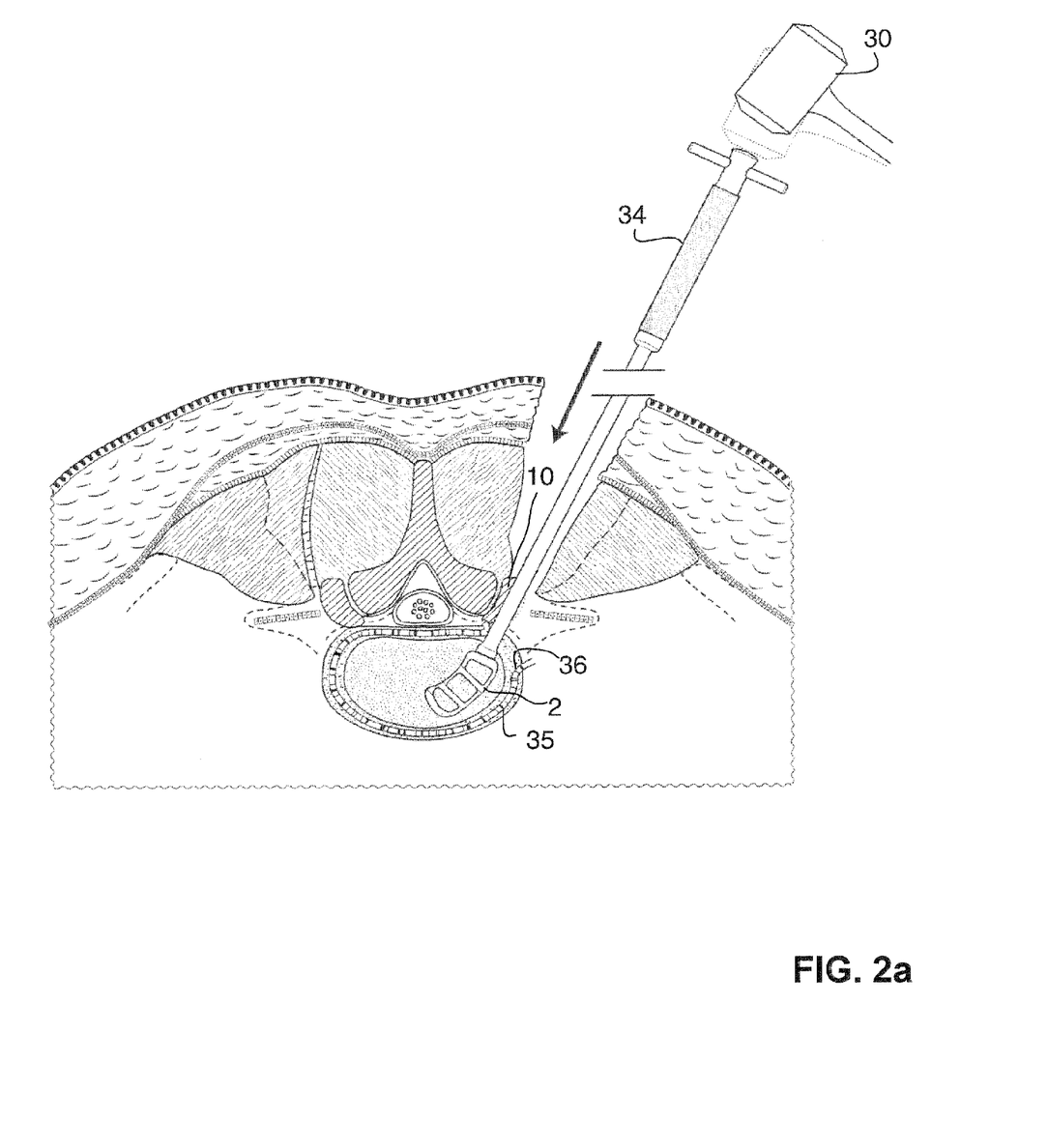
Figure 2B:
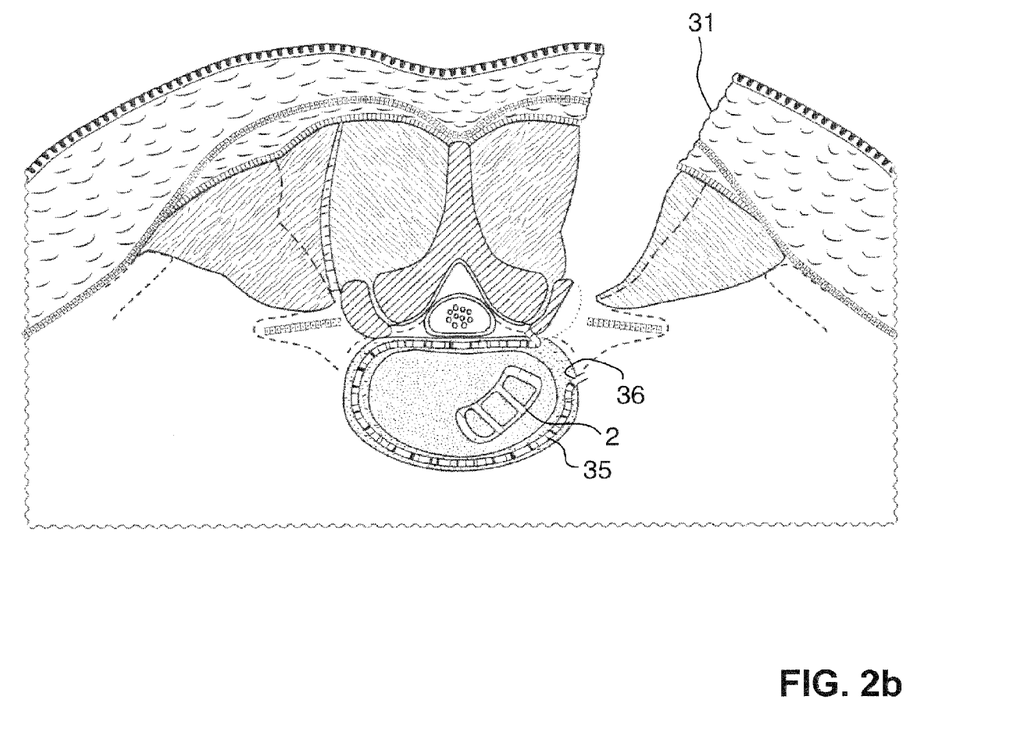
Figure 3A:
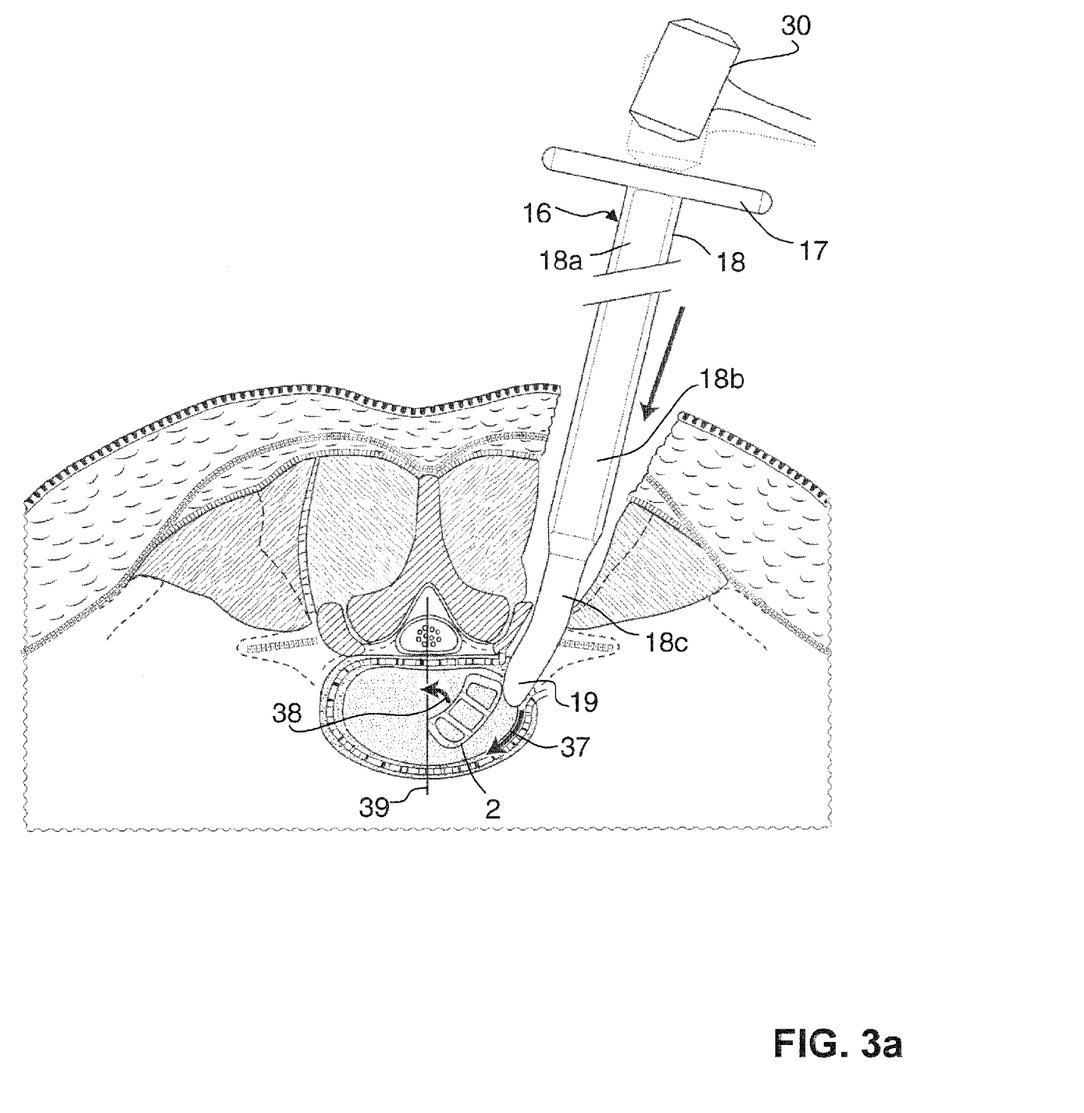

As shown in FIG. 2, the first cage 2 is inserted into the interdisc space 9 through the opening 11 until a front wall 27 reaches the midline 39 (FIG. 3*a*). The instrument for inserting the first cage 2 may be a well-known inserter 34. Percussion with a hammer 30 upon the inserter 34 moves the cage 2 into the position shown in FIG. 2*b*.

Figure 3B:
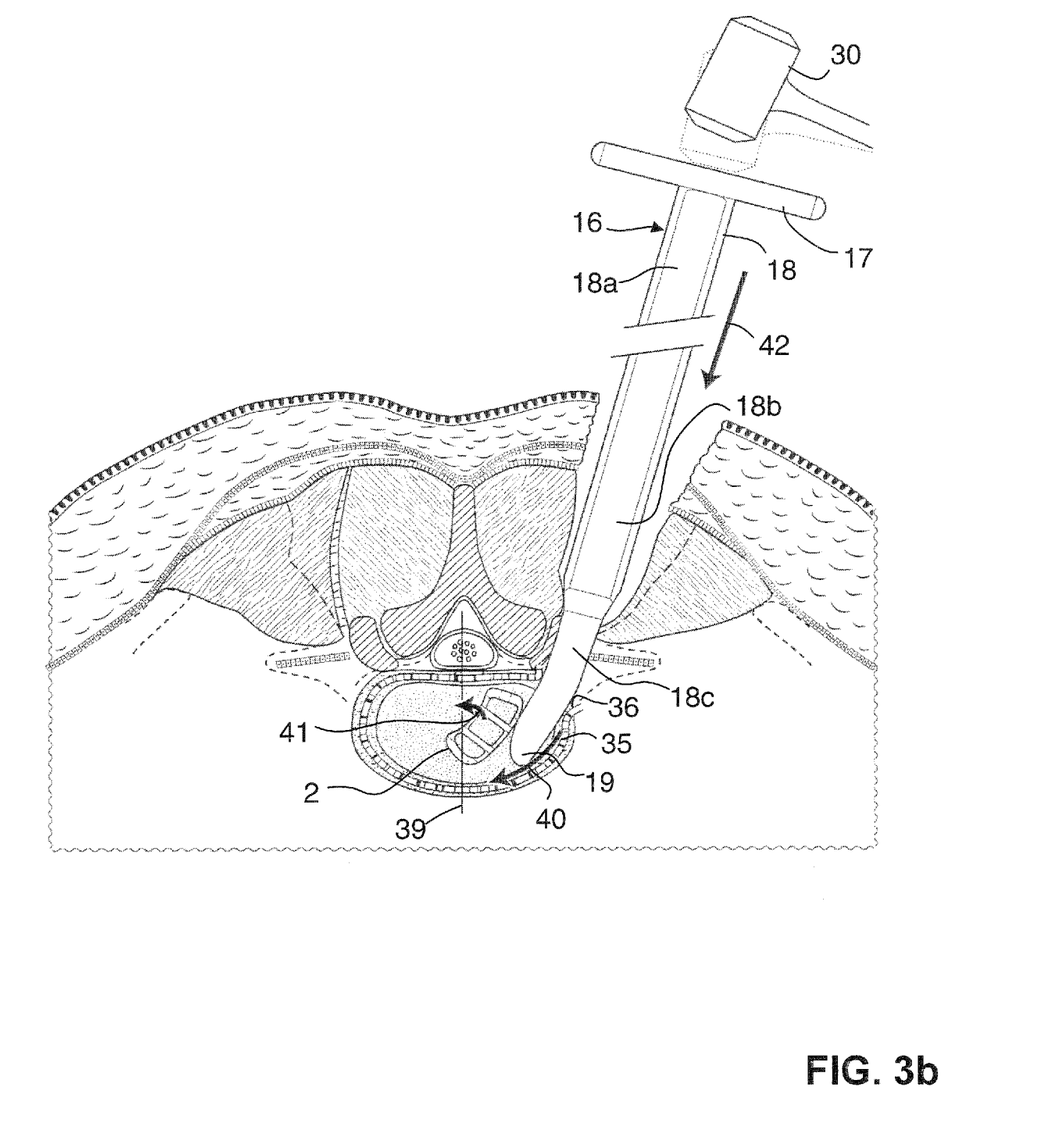
Figure 3C:
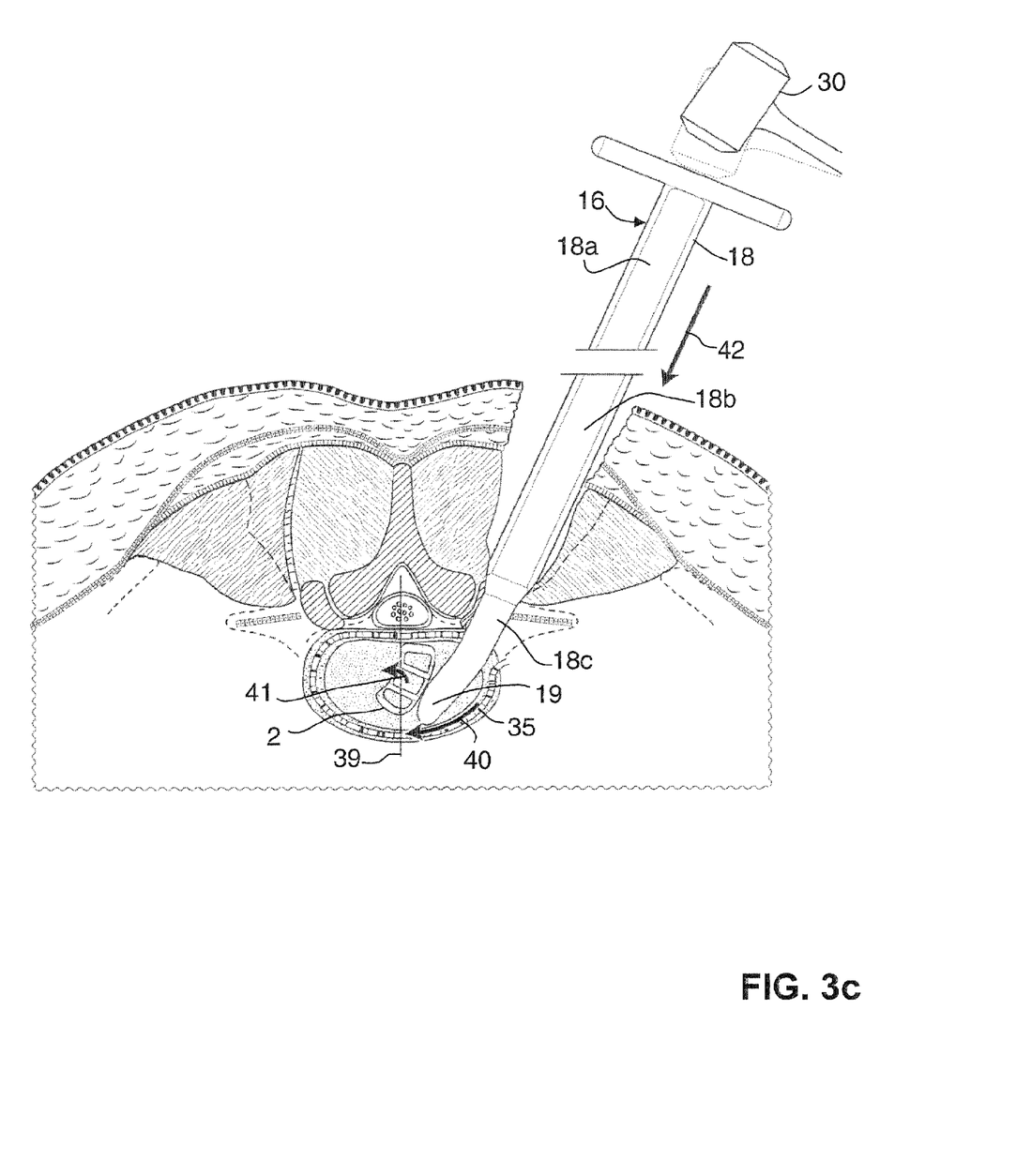

The cage 2 is now moved using the positioning instrument 16 as illustrated in FIGS. 3*a* to 3*c*. The positioning instrument 16 comprises a handle 17, a shaft 18, having a straight proximal part 18*a*, a tapered middle part 18*b*, and a curved distal part 18*c*. The distal part 18*c* is provided with a concave inner surface 22 (FIG. 8) and a convex outer surface 23. The positioning instrument 16 first contacts the first cage 2 with a rounded tip 19 at a curved outer side 25, as shown in FIG. 8. The tip 19 then moves with the concave surface 22 along the outer side 25 until the cage 2 reaches the position shown in FIG. 3*b*. The cage 2 contacts now the positioning instrument 16 at the concave surface 22 and passes the midline 39 as shown in FIG. 3*c*. The movement of cage 2 is indicated with arrows 38 and 41 and the movement of the tip 19 with arrows 37 and 40. The FIGS. 3*b* and 3*c* clearly show that the distal part 18*c* is curved. Due to the curved form of the tip 19, the positioning instrument 16 buttress against the natural ring apophysis 8. When the hammer 30 impacts the handle 13, percussion force follows the long access of the instrument shaft 18, as shown with arrow 42 in FIGS. 3*b* and 3*c*, and transforms into a lateral force, translating the posterior aspect of cage 2 medial and away from the small opening 36 into the interspace 9.

Figure 4A:
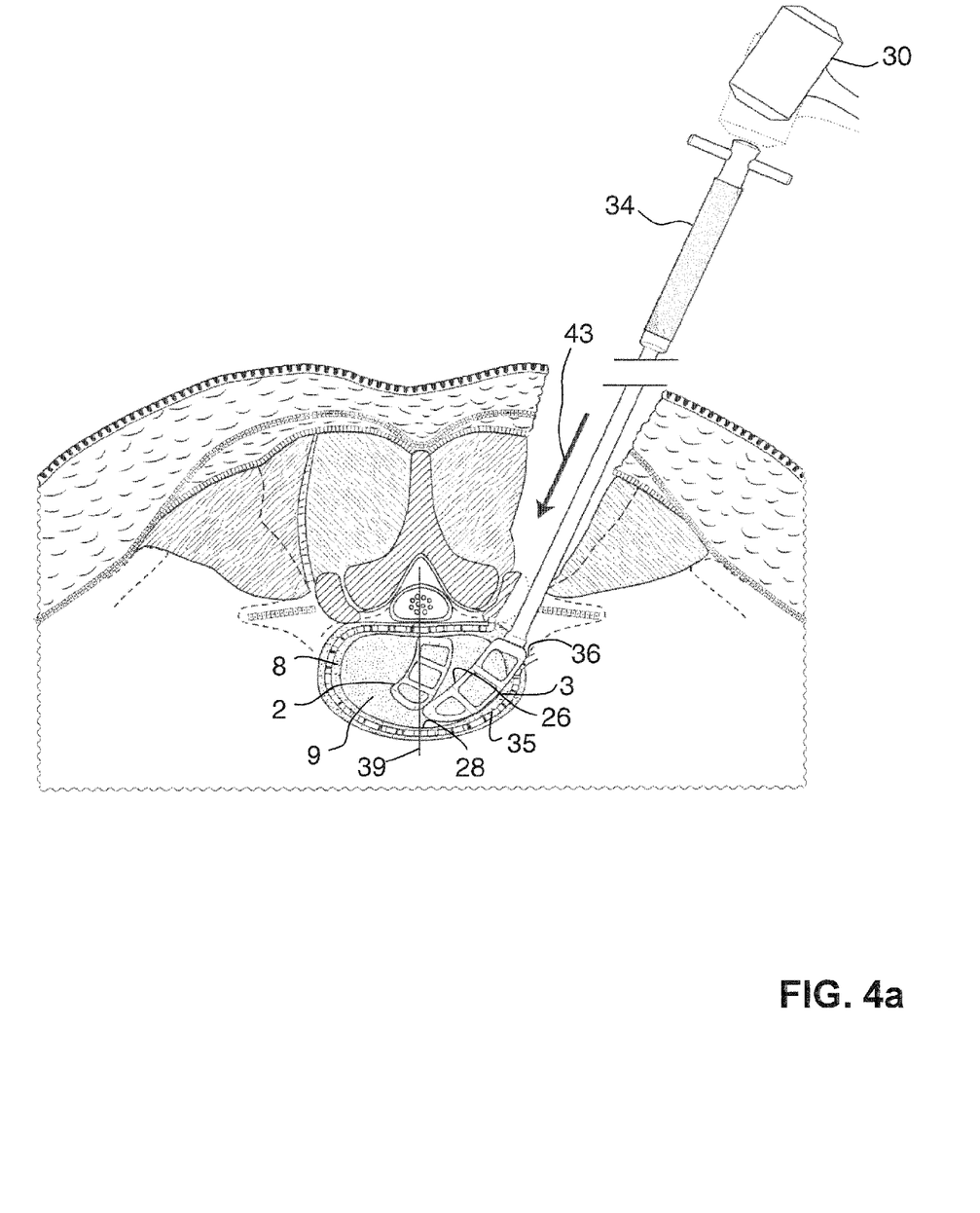
Figure 4B:
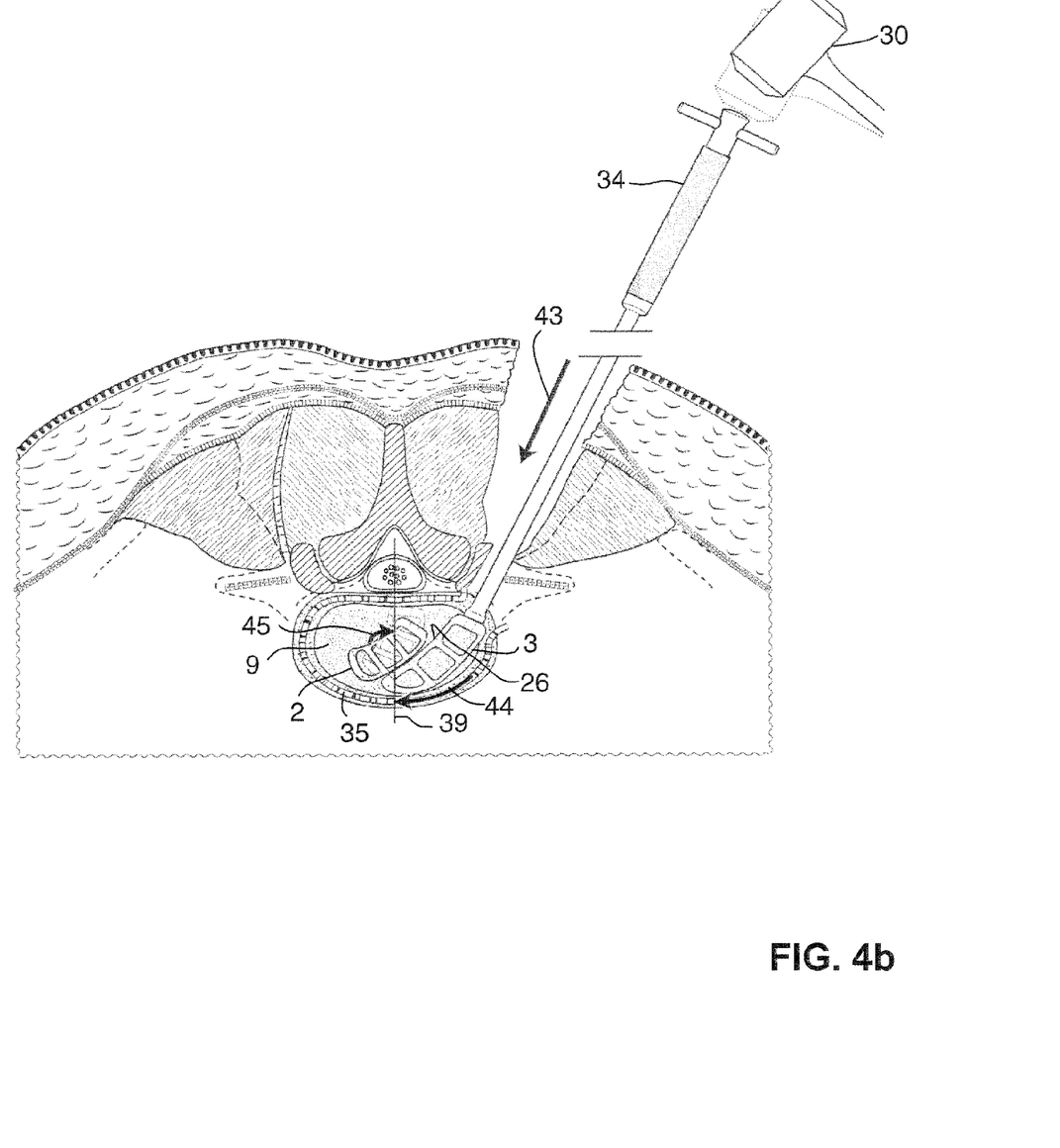
Figure 5:
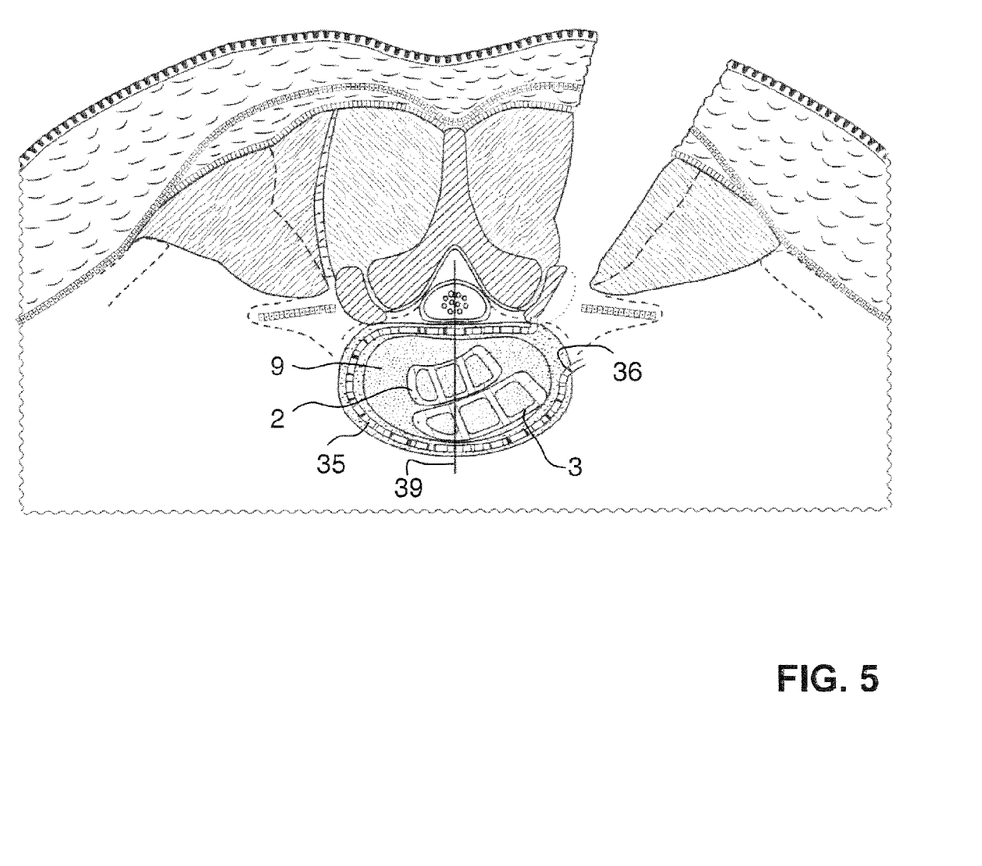
Figure 6:
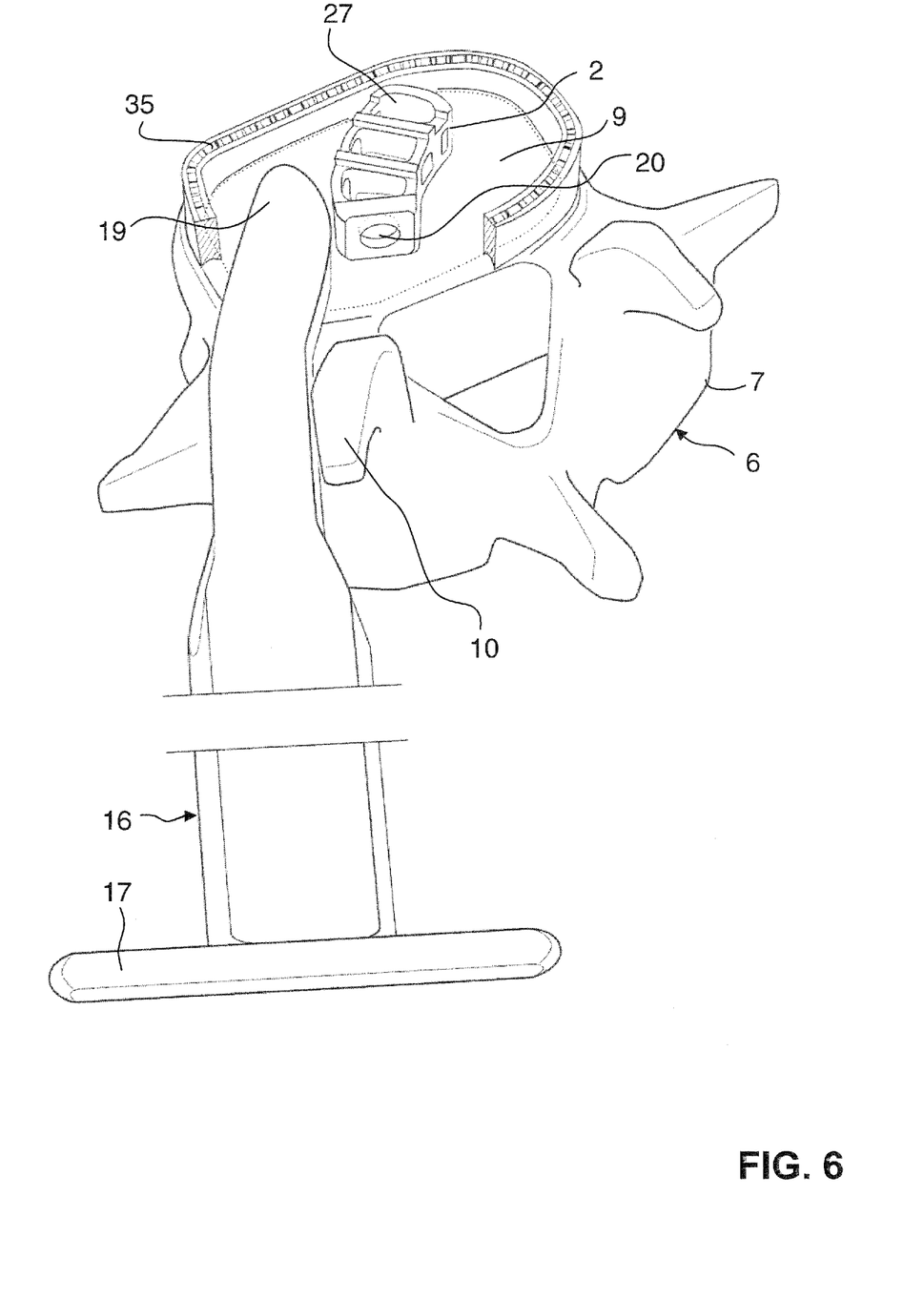

In the next step the positioning instrument 16 is retracted and the second cage 3 is inserted using the implant inserter 34. This implant inserter 34 is connected with the second cage 3 at a threaded opening. The second cage 3 has at its distal end a curved outer side 28 as shown in FIG. 4 and is guided with this outer side 28 at the ring apophysis 8 of the vertebra 7. As the second cage 3 is moved along the ring apophysis 8 it pushes the first cage 2 with a concave inner side 26 in its final anatomical location. Both cages 2 and 3 are now located in the interdisc space 9, so that bone growth may fuse the implant 1 to the adjacent vertebrae. The instrumentation set therefore allows the insertion of two cages 2 and 3 through a relatively small incision in the interdisc space in a simple jet safe procedure.

| REFERENCE NUMBERS | |
|---|---|
| 1 | implant |
| 2 | first cage |
| 3 | second cage |
| 4 | struts |
| 5 | openings |
| 6 | spine |
| 7 | vertebra |
| 8 | ring apophysis |
| 9 | interdisc space |
| 10 | superior articular process |
| 11 | opening |
| 12 | spacer |
| 13 | handle |
| 14 | shaft |
| 14a | proximal part |
| 14b | middle part |
| 15 | distal |
| 16 | positioning instrument |

-continued

| REFERENCE NUMBERS | |
|---|---|
| 17 | handle |
| 18 | shaft |
| 18a | proximal part |
| 18b | middle part |
| 18c | distal part |
| 19 | tip |
| 20 | threaded opening |
| 21 | surface |
| 22 | surface |
| 23 | surface |
| 24 | rear wall |
| 25 | outer side |
| 26 | inner side |
| 27 | front wall |
| 28 | outer side |
| 29 | inner side |
| 30 | hammer |
| 31 | incision |
| 32 | arrow |
| 33 | arrow |
| 34 | inserter |
| 35 | annulus fibrosus |
| 36 | opening |
| 37 | arrow |
| 38 | arrow |
| 39 | midline |
| 40 | arrow |

The invention claimed is:

1. A spinal implant and instrument of an instrument set used to prepare a disc space and to insert the implant into said disc space, wherein:
the implant comprises a first cage and a second cage, and
the instrument comprises a distal end configured to push the first cage that is inserted first into the disc space laterally in its proper anatomical location, so that the second cage can be inserted, wherein said distal end has a tip, which is curved and the distal end has a shape of a curved finger and comprises a curved inner side adapted to contact an outer curved side of the first cage,
the first cage and the second cage each have a curved inner side and a curved outer side and the curved outer side of the first cage is configured to contact the curved inner side of the second cage, and
the second cage has a wedge shaped front part.

2. The spinal implant and instrument of an instrument set according to claim 1, wherein the cage to be inserted first is shorter than the second cage.

3. The spinal implant and instrument of an instrument set according to claim 1, wherein the instrument is configured to be inserted with its distal end into the same opening as the first cage and the second cage, and the first cage and the second cage and the instrument are insertable in said opening at an angle of 20° to 60° to the midline.

4. The spinal implant and instrument of an instrument set according to claim 3, wherein the instrument is insertable at approximately 30° to the midline.

5. The spinal implant and instrument of an instrument set according to claim 1, wherein the instrument has a shaft with a tapered middle part and a straight proximal part.

6. A spinal implant and instrument of an instrument set used to prepare a disc space and to insert the implant into said disc space, wherein:
the implant comprises a first cage and a second cage, the first cage and the second cage each have a curved inner side and a curved outer side and the curved outer side of the first cage is configured to contact the curved inner side of the second cage, and the instrument comprises a handle and a shaft with a distal end, wherein a percussion force applied to the handle follows the shaft and transforms into a lateral force and wherein the distal end is configured to itself push the first cage that is already inserted into the disc space laterally in its proper anatomical location, so that the second cage can be inserted, wherein said distal end has a tip, which is curved and the distal end has a shape of a curved finger and comprises a curved inner side adapted to contact the outer curved side of the first cage, and
the second cage has a wedge shaped front part.

* * * * *